(12) United States Patent
Freudiger

(10) Patent No.: US 8,282,672 B2
(45) Date of Patent: Oct. 9, 2012

(54) FRICTIONAL SCREW-ROD CONNECTION HAVING AN INDIRECT FORM-LOCKING PORTION

(75) Inventor: Stefan Freudiger, Bremgarten (CH)

(73) Assignee: Bird Biedermann AG, Sachseln (CH)

( * ) Notice: Subject to any disclaimer, the term of this patent is extended or adjusted under 35 U.S.C. 154(b) by 142 days.

(21) Appl. No.: 11/512,461

(22) Filed: Aug. 29, 2006

(65) Prior Publication Data
US 2007/0093820 A1 Apr. 26, 2007

Related U.S. Application Data

(60) Provisional application No. 60/738,695, filed on Nov. 21, 2005.

(30) Foreign Application Priority Data

Aug. 29, 2005 (CH) ....................................... 1409/05

(51) Int. Cl.
*A61B 17/70* (2006.01)
(52) U.S. Cl. ........................................ 606/267; 606/262
(58) Field of Classification Search ................ 606/59, 606/300, 246–279; 403/87, 230
See application file for complete search history.

(56) References Cited

U.S. PATENT DOCUMENTS

| | | | | |
|---|---|---|---|---|
| 5,005,562 A | * | 4/1991 | Cotrel | 606/330 |
| 5,154,719 A | | 10/1992 | Cotrel | |
| 5,257,993 A | * | 11/1993 | Asher et al. | 606/300 |
| 5,261,912 A | * | 11/1993 | Frigg | 606/302 |
| 5,282,863 A | * | 2/1994 | Burton | 606/254 |
| 5,360,431 A | * | 11/1994 | Puno et al. | 606/265 |
| 5,443,467 A | | 8/1995 | Biedermann et al. | |
| 5,520,689 A | | 5/1996 | Schläpfer et al. | |
| 5,545,165 A | | 8/1996 | Biedermann et al. | |
| 5,562,663 A | | 10/1996 | Wisnewski et al. | |
| 5,658,284 A | * | 8/1997 | Sebastian et al. | 606/278 |
| 5,716,356 A | | 2/1998 | Biedermann et al. | |
| 6,117,137 A | * | 9/2000 | Halm et al. | 606/308 |
| 6,224,598 B1 | | 5/2001 | Jackson | |
| 6,302,410 B1 | | 10/2001 | Wentworth et al. | |
| 6,440,134 B1 | | 8/2002 | Zaccherotti et al. | |
| 6,478,797 B1 | * | 11/2002 | Paul | 606/264 |
| 6,540,748 B2 | | 4/2003 | Lombardo et al. | |
| 6,554,834 B1 | | 4/2003 | Crozet et al. | |
| 6,565,565 B1 | * | 5/2003 | Yuan et al. | 606/272 |

(Continued)

FOREIGN PATENT DOCUMENTS

CA 2133484 1/1995

(Continued)

OTHER PUBLICATIONS

International Search Report for Swiss Application No. 1409/05 dated Jun. 4, 2006, 3 pp.

(Continued)

*Primary Examiner* — Eduardo C Robert
*Assistant Examiner* — Steven Cotroneo
(74) *Attorney, Agent, or Firm* — Christie, Parker & Hale, LLP

(57) ABSTRACT

A spinal column implant for elastic stabilization of vertebrae, includes a pedicle screw and an elastic rod which is anchored in a frictional fashion in a receptacle of pedicle screws by means of a filling piece, and a clamping element. The frictional connection is supported additionally by an indirect form-fit portion.

28 Claims, 4 Drawing Sheets

U.S. PATENT DOCUMENTS

| | | | |
|---|---|---|---|
| 6,652,526 | B1 | 11/2003 | Arafiles |
| 6,783,527 | B2 | 8/2004 | Drewry et al. |
| 7,125,410 | B2 | 10/2006 | Freudiger |
| 7,731,749 | B2 | 6/2010 | Biedermann et al. |
| 8,157,843 | B2 | 4/2012 | Biedermann et al. |
| 2001/0020168 | A1* | 9/2001 | Hermann et al. ............... 606/61 |
| 2003/0032957 | A1* | 2/2003 | McKinley ..................... 606/61 |
| 2003/0083657 | A1 | 5/2003 | Drewry et al. |
| 2003/0125742 | A1* | 7/2003 | Yuan et al. ..................... 606/61 |
| 2003/0187439 | A1 | 10/2003 | Biedermann et al. |
| 2003/0220642 | A1* | 11/2003 | Freudiger ..................... 606/61 |
| 2003/0220643 | A1 | 11/2003 | Ferree |
| 2004/0138660 | A1 | 7/2004 | Serhan |
| 2004/0172025 | A1 | 9/2004 | Drewry et al. |
| 2005/0096659 | A1 | 5/2005 | Freudiger |
| 2005/0131410 | A1 | 6/2005 | Lin |
| 2007/0093821 | A1 | 4/2007 | Freudiger |
| 2008/0114404 | A1 | 5/2008 | Matthis et al. |
| 2010/0286731 | A1 | 11/2010 | Biedermann et al. |

FOREIGN PATENT DOCUMENTS

| | | |
|---|---|---|
| DE | 4234118 A1 | 4/1994 |
| DE | 4307576 C1 | 4/1994 |
| DE | 4425357 A1 | 2/1996 |
| EP | 0689798 B1 | 1/1996 |
| EP | 0 669 109 B1 | 5/1999 |
| EP | 1364622 B1 | 11/2003 |
| EP | 1527742 A1 | 5/2005 |
| FR | 2739548 A1 | 4/1997 |
| JP | 06038977 | 2/1994 |
| JP | 09-503148 A | 3/1997 |
| JP | 2003-339726 A | 12/2003 |
| WO | WO 95/01132 A1 | 1/1995 |
| WO | WO 98/27884 A1 | 7/1998 |
| WO | WO 03/015648 A1 | 2/2003 |

OTHER PUBLICATIONS

English Translation of Facts and Grounds of Opposition to the European Patent No. 1 759 646, Application No. 06 018 027.0 of Patent Proprietor Bird Biedermann AG, 7 pages.
European Search Report for European Application No. 05025161.0-2318 dated Mar. 21, 2006 and mailed Apr. 4, 2006, 6 pp.
English translation of JP Office action, dated Oct. 15, 2010, Corresponding to Patent Application No. 2006-230330.
JP Patent Abstract of 2003-290246, dated Oct. 14, 2003 (Corresponds to US 2003/0187439).
EP Interim Decision dated Jul. 19, 2010 in counterpart EP Application 06018027.0-2310, English Translation.
current claims for U.S. Appl. No. 12/789,162 (3 sheets).
OA dated May 11, 2011 for U.S. Appl. No. 12/789,162 (9 sheets).
OA dated Jan. 4, 2012 for U.S. Appl. No. 12/789,162 (9 sheets).
current claims for U.S. Appl. No. 11/520,286 (6 sheets).
OA dated Dec. 22, 2008 for U.S. Appl. No. 11/520,286 (10 sheets).
OA dated May 1, 2009 for U.S. Appl. No. 11/520,286 (14 sheets).
OA dated Sep. 23, 2009 for U.S. Appl. No. 11/520,286 (10 sheets).
OA dated Apr. 9, 2010 for U.S. Appl. No. 11/520,286 (12 sheets).
OA dated Mar. 24, 2009 for U.S. Appl. No. 11/642,566 (7 sheets).
OA dated Oct. 23, 2009 for U.S. Appl. No. 11/642,566 (10 sheets).
OA dated Jun. 10, 2011 for U.S. Appl. No. 11/642,566 (10 sheets).
current claims for U.S. Appl. No. 11/854,508 (5 sheets).
OA dated Nov. 27, 2009 for U.S. Appl. No. 11/854,508 (13 sheets).
OA dated May 21, 2010 for U.S. Appl. No. 11/854,508 (15 sheets).
OA dated Dec. 7, 2010 for U.S. Appl. No. 11/854,508 (16 sheets).
OA dated May 25, 2011 for U.S. Appl. No. 11/854,508 (3 sheets).
OA dated Jan. 17, 2012 for U.S. Appl. No. 11/854,508 (13 sheets).
OA dated Jun. 1, 2012 for U.S. Appl. No. 11/854,508 (12 sheets).

* cited by examiner

FRICTIONAL SCREW-ROD CONNECTION HAVING AN INDIRECT FORM-LOCKING PORTION

CROSS-REFERENCE TO RELATED APPLICATION(S)

The present disclosure claims the benefit of U.S. Provisional Patent Application Ser. No. 60/738,695, filed Nov. 21, 2005, and claims priority from Swiss Patent Application 1409/05, filed Aug. 29, 2005, the entire disclosures of which are incorporated herein by reference.

BACKGROUND

The present disclosure relates to a dynamic stabilizing system for spinal columns capable of stabilizing the spinal column without spinal fusion.

A multitude of rod/screw connections is available for metallic rods and used mainly in fusion operations (spinal fusion). There are only a few elastic systems that only support and stabilize, but do not fuse, the spinal segments and, thus, there are only a few devices for attaching the elastic connection elements to the pedicle screws.

As a matter of principle, rod/screw connections that are suitable for metallic rods are not necessarily also suitable for elastic connection elements since elastic rods made of plastic material, for example, possess different properties than rods made of metal that are stiffer by comparison. Accordingly, elastic rods made of plastic material cannot be simply clamped in a lasting fashion by means of frictional or force-fit connection since they usually are capable of reducing the clamping force by flowing. Consequently, there is a need for connection concepts comprising, aside from a possible frictional-type clamping, a contribution by form-fit which they attain for example by local elastic or plastic deformation.

WO 95/01132 (Schläpfer et al.) can achieve increased pressure in the contact zone by means of a sphere in the clamping screw. DE 4234118 A1 (Harms et al.) can achieve increased pressure in the contact zone by means of the edge of the hollow fixation screw. U.S. Pat. No. 5,005,562 (Cotrel) can achieve increased pressure in the contact zone by means of a circular toothed profile on the clamping screw. WO 03/015648 A1 (McKinley) can achieve increased pressure in the contact zone by means of teeth under the hat-shaped clamping screw. Even though the special features of the above-noted references can achieve increased pressure in the contact zone and therefore elastic or plastic, as it may be, flowing locally at the rod surface, such increased pressure would be insufficient in the case of an elastic rod made of plastic material.

U.S. Pat. No. 6,117,137 (Halm et al.) comprises grooves at the lower rod receptacle in the screw head but these only serve to provide additional support against longitudinal displacements. Moreover, the side opposite from these grooves does not possess a matching complementary structure.

EP 0 689 798 B1 (Sebastián Bueno et al.) comprises a receptacle that is non-congruent ("egg-shaped") to a round rod which can increase the clamping force of a metal rod. Since this profile does not comprise a specifically matching shape on the opposite side, it is unsuitable for an elastic rod made of plastic material due to the risk of flowing and reduction of tension.

EP 1 364 622 B1 (Freudiger) and EP 1 527 742 A1 (Freudiger) comprise mutually geometrically matching form-fit anchorings and thus are suitable for connecting an elastic rod made of plastic material rod to a pedicle screw. However, the positioning of the grooved surfaces requires very precise insertion in order to prevent canting. Moreover, grooved surfaces do not allow for continuous positioning.

U.S. Pat. No. 6,478,797 B1 (Paul) and US 2003/0125742 A1 (Yuan et al.) both comprise filling pieces that allow for all-around clamping of the metal rod when inserted from above. However, neither of the two systems comprises surface structures in the area of clamping that would be suitable for an elastic rod made of plastic material by means of a sufficient form-fit contribution.

FR 2739548 (Huitema) comprises a grooved connection on part of the circumference of the metal rod. Since the bushing with the groove must be applied to the rod by pushing, the bushing is not suitable for an elastic rod made of plastic material due to the risk of jamming.

SUMMARY

The present disclosure is based on the tasks to connect an elastic rod made of plastic material with a continuous smooth surface in continuous and secure fashion to a bone or pedicle screw and, in the process, transfer tensile and compressive as well as shearing and torsional forces between neighboring vertebrae.

The solution to this task is characterized in that the connection is a combination of a direct frictional or force-fit connection and an indirect form-fit connection. The indirect form-fit is attained by local elastic or plastic deformation (by flowing, for example) of the plastic material. The expansion of the form-fit may be larger than the constriction of the elastic rod made of plastic material under the expected tensile forces. The volumes of prominences and recesses may be of similar or equal size such that the volume of the plastic rod in the connection zone approximately re-attains its original value upon completion of the flow process. The contact surface of the screw connection and the rod is a cage that can prevent the rod material from uncontrolled flowing-out and prevent an associated uncontrolled positional change of the rod.

Accordingly, the disclosed frictional screw/rod connection with indirect form-fit portion allows a smooth elastic rod made of plastic material to be connected to the head of a bone or pedicle screw such that the expected forces can be transferred lastingly and securely due to its application as a dynamic stabilization of the lumbar spinal column. As a result, the present disclosure combines a frictional connection, which can be positioned easily and continuously, with the reliability of a form-fit portion to the connection. However, the form-fit is generated only upon connection by utilizing the flow properties of an elastic plastic material. The present disclosure thus provides simple and secure handling of the system under surgical conditions.

In the following, the present disclosure is illustrated in more detail by means of the appended drawings, in which exemplary embodiments are shown. In the figures, the following is shown schematically:

BRIEF DESCRIPTION OF THE DRAWINGS

FIG. 6b is a top view of FIG. 6a.

FIG. 7b is a bottom view of the filling piece of FIG. 7a.

DETAILED DESCRIPTION

Figure 2:
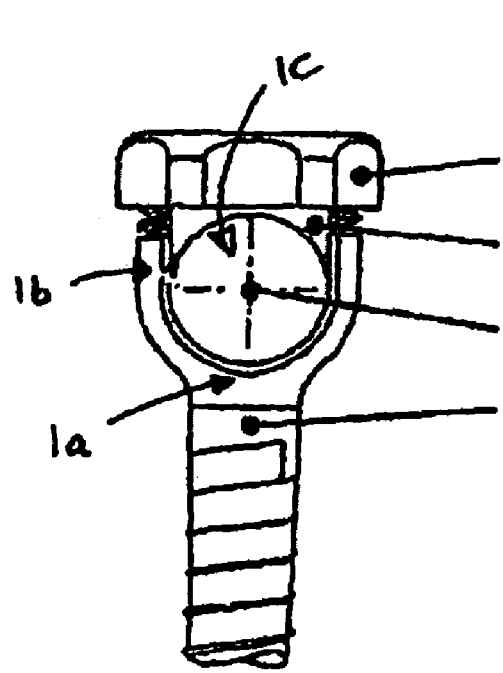
FIG. 2 shows an example of a round connection element in the receptacle of a pedicle screw with a filling piece and a clamping element.
Figure 3:
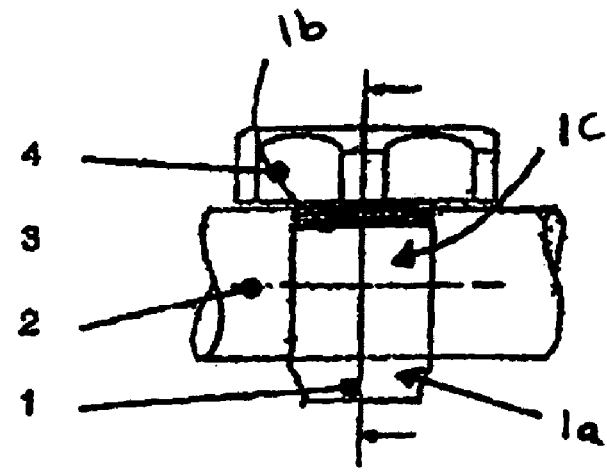
FIG. 3 shows a side view of FIG. 2.

Referring to FIGS. 2 and 3, a spinal column implant is shown which includes a plurality of bone screws 1 (only one screw is shown in FIGS. 2 and 3) and an elastic connection element 2 constructed from a plastic material that connects the bone screws 1. Each bone screw 1 includes a screw head portion 1a and a receptacle 1b for receiving the connection element 2 therein. The screw head portion 1a functions as a seat for the connection element when the connection element 2 is in the receptacle 1b. Each bone screw 1 further includes a filling piece 3 and a clamping element 4. The filling piece 3 can be guided in the receptacle 1b so as to be placed over the connection element 2. The connection element 2 can then be frictionally clamped in a space 1c in the receptacle 1b between the filling piece 3 and the screw head portion 1a by the clamping element 4. The contour of the space 1c deviates from the contour of the connection element 2.

Figure 1A:
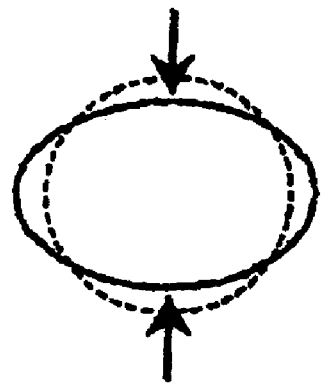
FIG. 1a shows a round cross-section not exposed to load and an oval cross-section exposed to load.
Figure 1B:
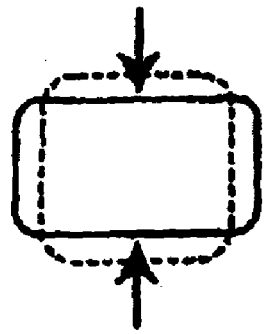
FIG. 1b shows a square cross-section not exposed to load and a rectangular cross-section exposed to load.
Figure 1C:
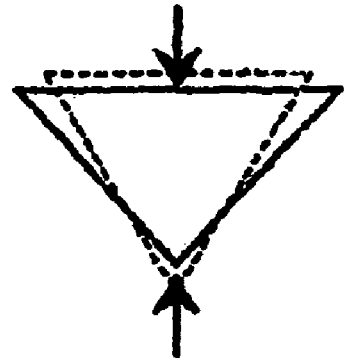
FIG. 1c shows a triangular cross-section not exposed to load and a triangular cross-section with broadened base exposed to load.

Referring to FIGS. 1a-1c, the connection element 2 may be a rod that can have any cross sectional shape. For example, the connection element 2 may have a circular cross section as shown in FIG. 1a, a square cross section as shown in FIG. 1b, or a triangular cross section as shown in FIG. 1c. The connection element 2 can be constructed from an elastic plastic material so as to provide the herein described contour deviation. An example of an elastic plastic material is PCU (Polycarbonate Urethane). However, other elastic-plastic materials may be used for the connection element 2. Additionally, the connection element 2 can have a smooth and continuous outer surface. FIG. 1a shows, for example, a round cross-section for the connection element 2 that is converted into an oval cross section due to the opposing forces shown. FIG. 1b shows, for example, a square cross-section for the connection element 2 that is converted into a rectangular cross section due to the opposing forces shown. FIG. 1c shows, for example, a triangular cross section for the connection element 2 that is converted into a triangular cross section with a more acute base angle due to the opposing forces shown. Thus, the elastic plastic construction of the connection element 2 provides for deformation of the connection element 2 due to the difference between the contour of the space 1c and the contour of the connection element 2 when the connection element 2 is clamped in the receptacle 1b between the screw head portion 1a and the filling piece 3.

Figure 6A:
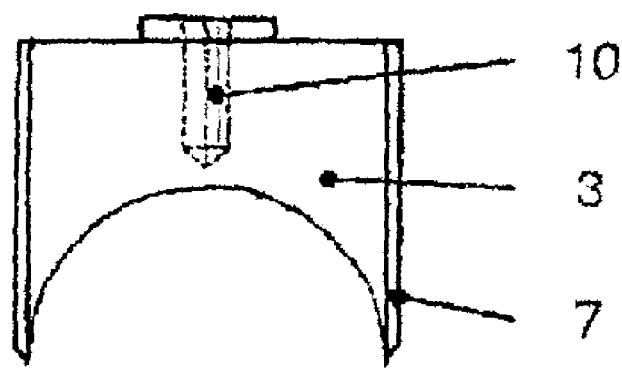
FIG. 6a shows a filling piece with an exemplary receptacle for a counter-pressure device.
Figure 6B:
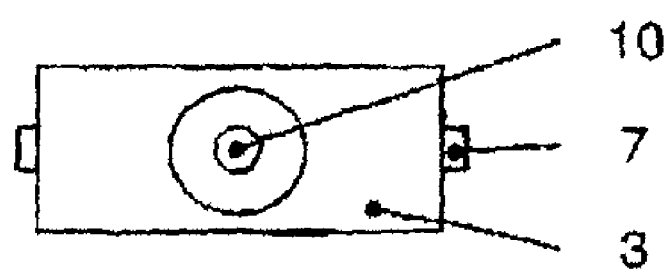
Figure 6C:
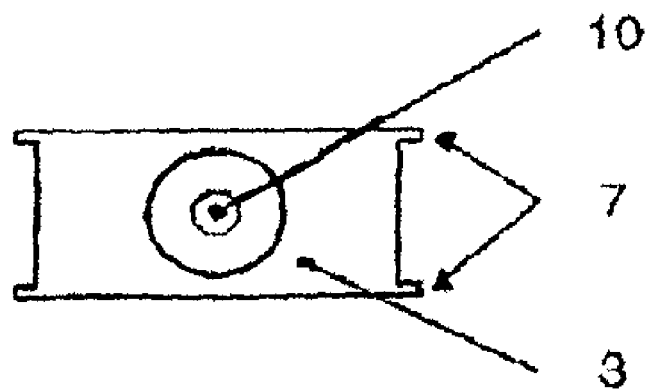
FIG. 6c is the same top view as FIG. 6b though with an alternative lateral guidance.

The clamping element 4 may be any type of clamping element 4 that is known to those of ordinary skill in the art. For example, the clamping element 4 may be a threaded nut that can be screwed onto the upper part of the screw 1. The filling piece 3 may be in any shape so as to provide the clamping of the connection element 2. In the disclosed example, the lower part of the filling piece 3 is receptacle shaped or recess shaped to receive the connection element 2. As shown in FIGS. 6a-6c, the filling piece 3 may also include lateral guides 7 that can engage corresponding recesses (not shown) in the receptacle 1b to guide the filling piece 3 in the receptacle 1b. A holding instrument may be provided to hold the filling piece 3. The filling piece 3 may include a receptacle for a holding instrument 10.

The deviation in the contour of the space 1c may be near the lower part of the receptacle 1b on the screw head portion 1a and near the upper part of the receptacle 1b on the filling piece 3. The deviation in the contour of the space 1c may be in the area near the lateral portions of the receptacle 1b. Furthermore, the deviations in the contour of the space 1c may be in one or more other portions of the space 1c transverse to the longitudinal axis of the connection element 2 in the same plane or in different planes. Additionally, the entire contour of the space 1c may deviate rather than local deviations to provide overall deformation of the connection element 2 as shown in FIGS. 1a-1c due to clamping forces exerted on the connection element 2.

Figure 4:
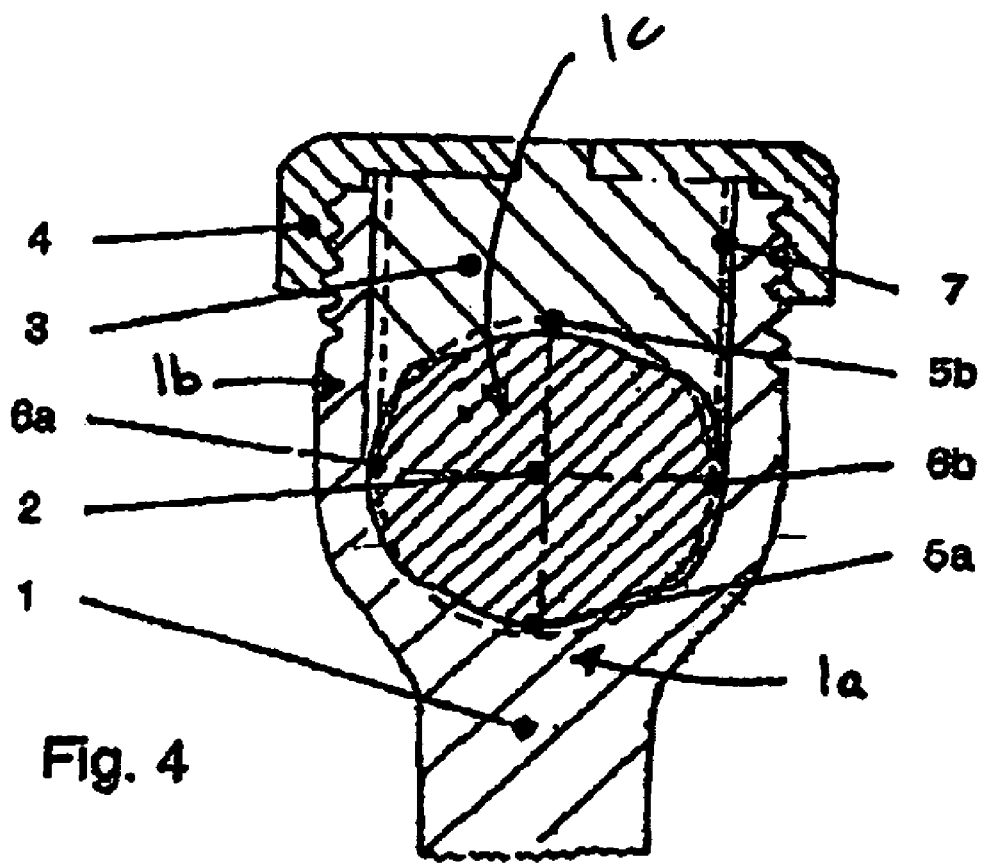
FIG. 4 shows a sectional view of FIG. 2 with local deviations from the cross-section of the connection element along the receptacle.

The contour deviations of the space 1c may be prominent deviations or recessed deviations. For example, the space 1c may have prominent upper and lower deviations and recessed lateral deviations. The prominent deviations may be formed by ribs, pegs, and/or other projections on the screw head portion 1a, the receptacle 1b and/or the filling piece 3. The recessed deviations in the contour of the space 1c may be formed by recessed portions of the space 1c. FIG. 4 shows a sectional view of FIG. 2, in which one or more portions of the contour of the space 1c include deviations. In FIG. 4, the space 1c at the bottom of the receptacle 1b at the screw head portion 1a includes an elevated rib 5a and the bottom of the filling piece 3 inside the receptacle 1b includes an elevated rib 5b. In FIG. 4, the ribs 5a and 5b provide prominent deviations of the contour of the space 1c. The contour of the space 1c can also include recessed deviations along the lateral portions of the space 1c, which are shown as a left recess 6a and a right recess 6b in FIG. 4. The contour of the space 1c could have both prominent deviations and recessed deviations.

The connection element 2 can be compressed in the space 1c upon fastening the clamping element 4. Before fastening of the clamping element 4 the filling piece 3 is guided downward in the receptacle 1b along the lateral guides 7 and onto the connection element 2. Then, the clamping element 4 can be fastened. Accordingly, the downward pressing by the filling piece 3 causes the rib 5a and the rib 5b to impinge upon the connection element 2 to provide recessed compression of the connection element 2 around the area of the ribs 5a and 5b. The compression of the connection element 2 by the filling piece 3 provides displacing of the material of the connection element 2 (e.g. by plastic flow), which can fill the recesses 6a and 6b. Accordingly, the deformation of the connection element 2 can provide a form-fit connection of the connection element 2 in the receptacle 1b.

Figure 5:
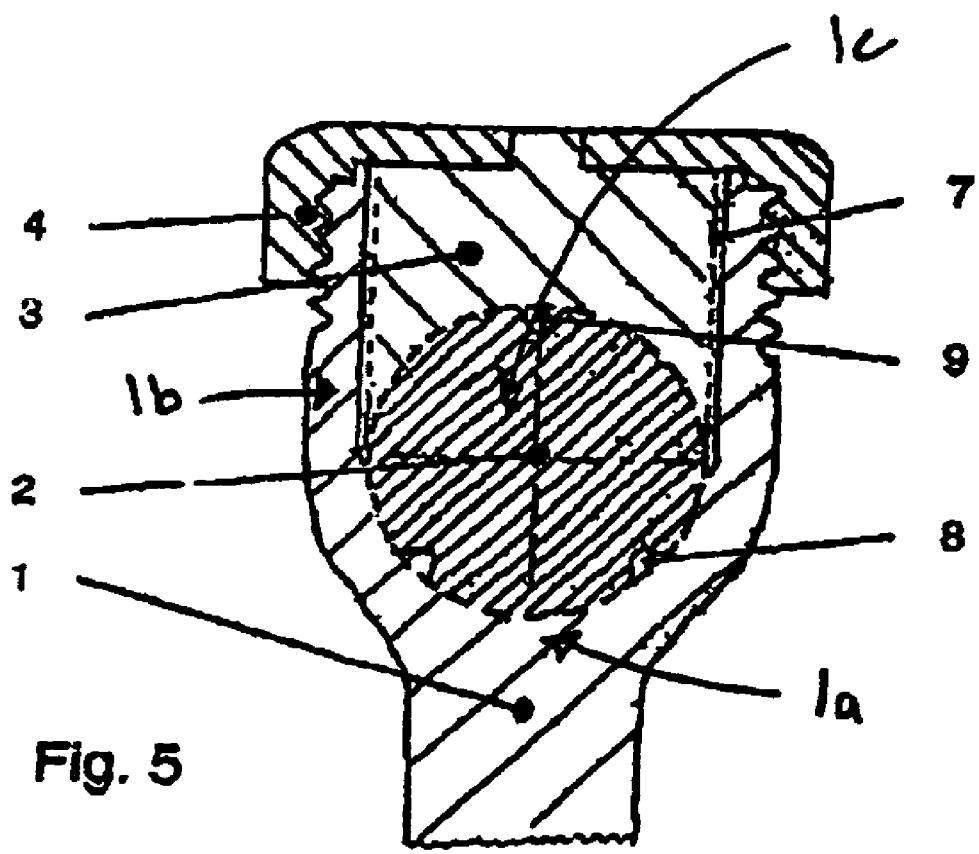
FIG. 5 shows a sectional view of FIG. 2 with peg-shaped deviations from the cross-section of the connection element along the receptacle on the screw and on the filling piece.

FIG. 5 shows a sectional view of FIG. 2, in which instead of the ribs 5a and 5b of FIG. 4, conical pegs 8 in the receptacle 1b at the screw head portion 1a and conical peg 9 on the filling piece 3 provide prominent deviations in the contour of the space 1c. The pegs 8 and 9 impinge upon the elastic plastic material of the connection element 2 to provide the recessed deformations of the connection element 2 around the pegs 8 and 9. Furthermore, as described above, the compression, i.e., recessed deformation, of the connection element 2 provides prominent deformation of the connection element to provide a form-fit connection in the space 1c. Although only two ribs and three pegs are shown in FIGS. 4 and 5, respectively, any number of pegs and/or ribs can be provided inside the receptacle 1b, on the screw head portion 1a and/or on the filling piece 3 to provide the above-described deviations in the contour of the space 1c and a resulting form-fit connection of the connection element 2 in the space 1c. Any projections, such as the ribs 5a, 5b and pegs 8, 9 can have similar or equal volume as the recesses 6a, 6b such that the clamped portion of the connection element 4 retains approximately the same volume before and after deformation upon completion of the flow process (i.e., plastic flow). Upon clamping of the connection element the frictional contact between the connection element 4 and the screw 1 in combination with the above-described form-fit connection prevents the material of the connection element 4 from uncontrolled flowing-out and any associated uncontrolled positional change of the connection element 4.

Figure 7A:
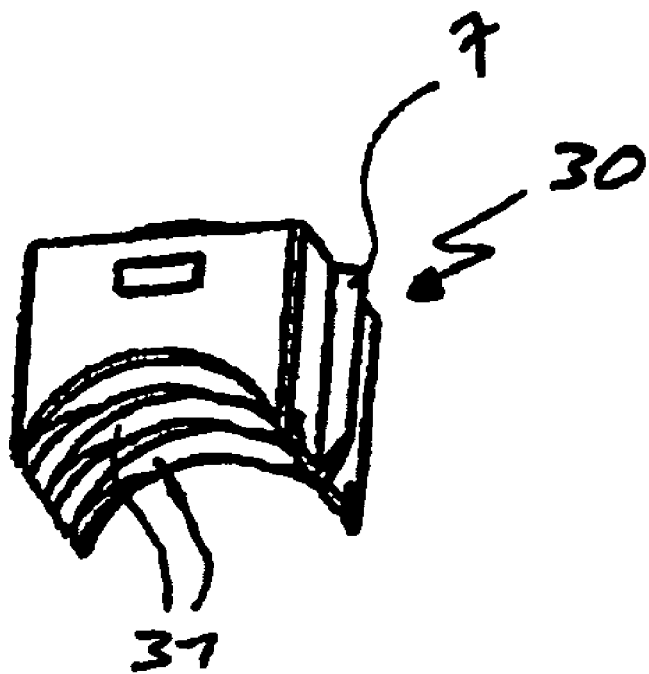
FIG. 7a is a perspective view of a filling piece according to an embodiment of the present disclosure.
Figure 7B:
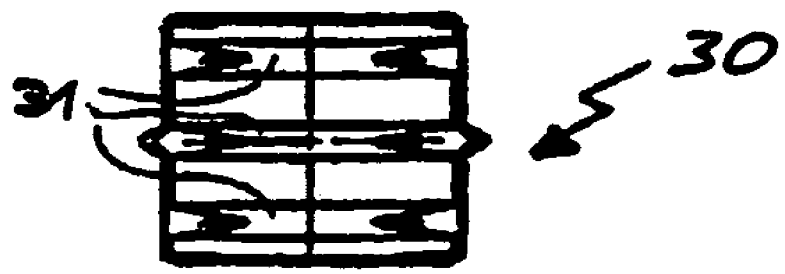

A modification of the filling piece is shown in FIGS. 7a and 7b. The filling piece 30 of FIGS. 7a and 7b differs from the filling piece 3 as described above in that a plurality of projecting ribs 31 are provided on the bottom of the filling piece 30, which is the side of the filling piece 30 that faces the connection element 2. The ribs 31 extend in a direction which is perpendicular to the longitudinal axis (not shown) of the connection element 2. The ribs 31 may be parallel to each other and may have the same distance from each other.

The receptacle 1b can also have at the screw head portion 1a, which is the seat of the connection element 2, a plurality of projecting ribs (not shown). The ribs also extend in a direction perpendicular to the longitudinal direction of the connection element 2. A plurality of ribs can be provided to create a smooth load distribution on the surface of the connection element 2. The number of the ribs can vary as compared to the ribs 31 of the filling piece.

The connection of the connection element 2 in the space 1c of each screw 1, which is attached to a corresponding vertebrae, provides the transfer of tensile and compressive as well as shearing and torsional forces between neighboring vertebrae. The connection of the connection element 2 to each screw 1 is a combination of a direct frictional or force-fit connection and an indirect form-fit connection. The indirect form-fit connection is attained by local elastic or plastic deformation (by flowing, for example) of the plastic material. The expansion of the form-fit may be larger than the constriction of the elastic connection element 2 made of plastic material under the expected tensile forces.

The above-described frictional connection with indirect form-fit contribution allows a smooth elastic connection element made of plastic material to be connected to a plurality of bone or pedicle screws of a spinal implant such that the expected forces generated by dynamic stabilization of the lumbar spinal column can be continuously and securely transferred to the elastic connection element made of plastic material. The indirect form-fit contribution to the connection is generated upon utilizing the plastic flow properties of the elastic connection element made of plastic material. The present disclosure thus provides simple and secure handling of the spinal implant system under surgical conditions.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A spinal column implant comprising:
    an elastic connection element formed from a plastic material and extending along a longitudinal axis, the connection element having a constant cross-section along the longitudinal axis;
    a plurality of bone anchoring elements, each bone anchoring element having a head portion defining a receptacle for the connection element, a filling piece configured to be located in the receptacle, and a clamping element, wherein the filling piece and the head portion have opposed seats that define a space therebetween in the receptacle configured to receive the connection element;
    wherein the clamping element is securable to the head portion to clamp a portion of the connection element in the space into a clamped position;
    wherein the seat of the filling piece defines a recess entirely through the filling piece such that the elastic connection element passes entirely through the filling piece when the elastic connection element and the filling piece are located in the receptacle of the bone anchoring element and the elastic connection element is seated in the recess;
    wherein at least one of a contour of the seat of the filling piece and a contour of the seat of the head portion deviate from a contour of the connection element;
    wherein the seats are movable relative to each other between a non-clamped position wherein both seats contact the connection element over a first surface area and the clamped position, closer together, wherein the seats contact the connection element over an increased surface area and the connection element is elastically deformed in the space between the seats; and
    wherein the elastic connection element permits movement of the plurality of bone anchoring elements relative to each other.

2. A spinal column implant according to claim 1, wherein laterally opposed surfaces defining the receptacle of the head portion deviate from the contour of the connection element.

3. A spinal column implant according to claim 2, wherein the contour deviations relative to the seat of the filling piece and the seat of the head portion are prominent and the deviations relative to the laterally opposed surfaces of the head portion are recessed.

4. The spinal column implant of claim 3, wherein the volume of the prominent contour deviations into the space is equal to the volume of the recessed contour deviations away from the space.

5. A spinal column implant according to claim 1, wherein the contour deviations are situated in one or more sections transverse to a longitudinal axis of the connection element, in the same plane or in different planes.

6. A spinal column implant according to claim 1, wherein the elastic connection element is a round rod.

7. A spinal column implant according to claim 1, wherein the connection element is made of polycarbonate urethane.

8. A spinal column implant according to claim 1, wherein the clamping element is a screw nut.

9. A spinal column implant according to claim 1, wherein the filling piece comprises a receptacle for a holding instrument.

10. A spinal column implant according to claim 1, wherein the filling piece is laterally guided in the receptacle by mating projections and recesses.

11. The spinal column implant of claim 1, wherein the connection element has a substantially smooth and continuous outer surface.

12. The spinal column implant of claim 1, wherein a volume of the portion of the connection element in the non-clamped position in the space is substantially equal to the volume of the portion of the connection element in the clamped position.

13. The spinal column implant of claim 1, wherein the recess of the seat of the filling piece is defined by a concave surface.

14. The spinal column implant of claim 13, wherein the concave surface is a cylindrical segment having an axis extending in the direction of the length of the filling piece.

15. The spinal column implant of claim 14, wherein the filling piece has a protrusion extending from the cylindrical segment into the recess.

16. The spinal column implant of claim 13, wherein the filling piece has a protrusion extending from the concave surface into the recess.

17. The spinal column implant of claim 16, wherein the protrusion is an elongated rib that is elongated in a direction transverse to the longitudinal axis of the elastic connection element when the elastic connection element is seated in the seat of the head portion.

18. The spinal column implant of claim 17 wherein the elongated rib is one of a plurality of elongated ribs, each elongated in a direction transverse to the longitudinal axis of the elastic connection element when the elastic connection element is seated in the seat of the head portion.

19. The spinal column implant of claim 16, wherein the seat of the head portion defines a concave surface and has a protrusion extending from the concave surface toward the filling piece.

20. The spinal column implant of claim 19, wherein the protrusion extending form the concave surface is an elongated rib that is elongated in a direction transverse to the longitudinal axis of the elastic connection element when the elastic connection element is seated in the seat of the head portion.

21. A spinal column implant comprising:
a plastically deformable connection element formed from a plastic material and extending along a longitudinal axis, the connection element having a constant cross-section along the longitudinal axis; and
a bone anchoring element comprising a head portion defining a receptacle configured to receive a section of the connection element, a filling piece configured to be located in the receptacle, and a clamping element, wherein the filling piece and the head portion have opposed seats that define a space therebetween in the receptacle configured to receive the connection element, and wherein the clamping element is configured to clamp the section of the connection element in the space into a clamped position;
wherein the seat of the filling piece defines a recess entirely through the filling piece such that the elastic connection element passes entirely through the filling piece when the elastic connection element and the filling piece are located in the receptacle of the bone anchoring element and the elastic connection element is seated in the recess;
wherein at least one of a contour of the seat of the head portion and a contour of the seat of the filling piece deviate from a contour of the connection element;
wherein the seats are movable relative to each other between a non-clamped position wherein both seats contact the connection element over a first surface area and the clamped position, closer together, wherein the seats contact the connection element over an increased surface area and the connection element is elastically deformed in the space between the seats, and
wherein the elastic connection element permits movement of a plurality of bone anchoring elements relative to each other.

22. A spinal column implant according to claim 21, wherein the connection element comprises polycarbonate urethane.

23. A spinal column implant according to claim 21, wherein laterally opposed surfaces defining the receptacle of the head portion deviate from the contour of the connection element.

24. A spinal column implant according to claim 21, wherein the connection element deforms by one or more prominent deformations and recessed deformations.

25. A spinal column implant according to claim 21, wherein a cross section of the connection element is any one of circular, square and triangular shaped.

26. A spinal column implant according to claim 21, wherein the filling piece is laterally guided in the receptacle by mating projections and recesses.

27. The spinal column implant of claim 21, wherein the contour of the seat of the filling piece deviates from the contour of the connection element.

28. The spinal column implant of claim 27, wherein the contour of the seat of the head portion deviates from the contour of the connection element.

* * * * *